(12) United States Patent
Kato

(10) Patent No.: US 12,168,076 B2
(45) Date of Patent: Dec. 17, 2024

(54) ABSORBENT ARTICLE

(71) Applicant: DAIO PAPER CORPORATION, Ehime (JP)

(72) Inventor: Chihiro Kato, Ehime (JP)

(73) Assignee: Daio Paper Corporation, Ehime (JP)

( * ) Notice: Subject to any disclaimer, the term of this patent is extended or adjusted under 35 U.S.C. 154(b) by 582 days.

(21) Appl. No.: 17/435,464

(22) PCT Filed: Jan. 27, 2020

(86) PCT No.: PCT/JP2020/002693
§ 371 (c)(1),
(2) Date: Sep. 1, 2021

(87) PCT Pub. No.: WO2020/195097
PCT Pub. Date: Oct. 1, 2020

(65) Prior Publication Data
US 2022/0160927 A1 May 26, 2022

(30) Foreign Application Priority Data

Mar. 27, 2019 (JP) .................................. 2019-060524

(51) Int. Cl.
*A61F 13/15* (2006.01)
*A61F 13/53* (2006.01)
(Continued)

(52) U.S. Cl.
CPC ........ *A61L 15/20* (2013.01); *A61F 13/15203* (2013.01); *A61F 13/537* (2013.01);
(Continued)

(58) Field of Classification Search
CPC ................ A61F 13/15; A61F 13/51113; A61F 2013/51117; A61F 13/51121; A61L 15/20
See application file for complete search history.

(56) References Cited

U.S. PATENT DOCUMENTS 5,753,257 A * 5/1998 DiPippo ................. A61L 15/46
424/769
5,885,267 A * 3/1999 Mishima ........... A61F 13/51305
604/378

(Continued)

FOREIGN PATENT DOCUMENTS

JP 2011-522672 8/2011
JP 2013-066614 4/2013
(Continued)

OTHER PUBLICATIONS

International Search Report for PCT/JP2020/002693, issued Mar. 24, 2020.

*Primary Examiner* — Leslie A Lopez
*Assistant Examiner* — Seth Han
(74) *Attorney, Agent, or Firm* — Andrus Intellectual Property Law, LLP

(57) ABSTRACT

To prevent or suppress roughness of the skin of a wearer by configuring an absorbent article so as to quickly absorb a body fluid into an absorber, for example, configuring a diaper so as to quickly absorb loose stool into an absorber. An absorbent article includes a liquid-holding absorber and a liquid pervious top sheet on a skin-facing surface side of the absorber. An absorbent Q mainly containing glycerin is provided on an intermediate sheet that transfers at least a body fluid that has passed through the top sheet to the absorber.

2 Claims, 7 Drawing Sheets

(51) Int. Cl.
    *A61F 13/534*     (2006.01)
    *A61F 13/537*     (2006.01)
    *A61L 15/20*     (2006.01)

(52) U.S. Cl.
    CPC .............. *A61F 2013/530868* (2013.01); *A61F 2013/5349* (2013.01)

(56) References Cited

U.S. PATENT DOCUMENTS

| | | | |
|---|---|---|---|
| 2012/0065605 A1* | 3/2012 | Takahashi | A61F 13/51456 604/372 |
| 2015/0297781 A1* | 10/2015 | Uda | A61L 15/20 604/366 |
| 2020/0038257 A1 | 2/2020 | Okada et al. | |

FOREIGN PATENT DOCUMENTS

| | | |
|---|---|---|
| JP | 2015-104646 | 6/2015 |
| JP | 2015104646 A * | 6/2015 |
| JP | 2018-000546 | 1/2018 |
| JP | 2018-102836 | 7/2018 |
| WO | 2018/180264 | 10/2018 |

* cited by examiner

[FIG.1]
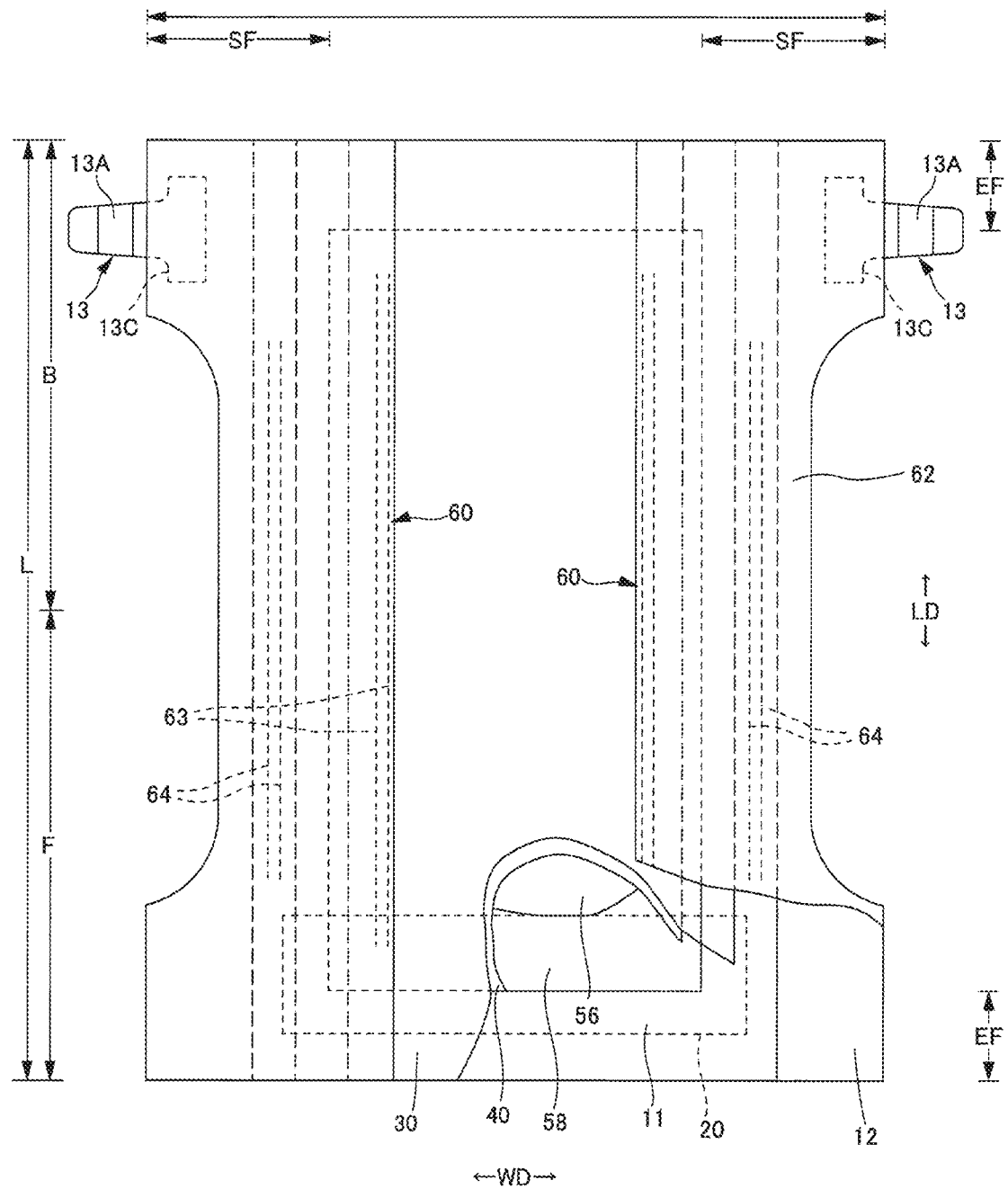

[FIG.2]
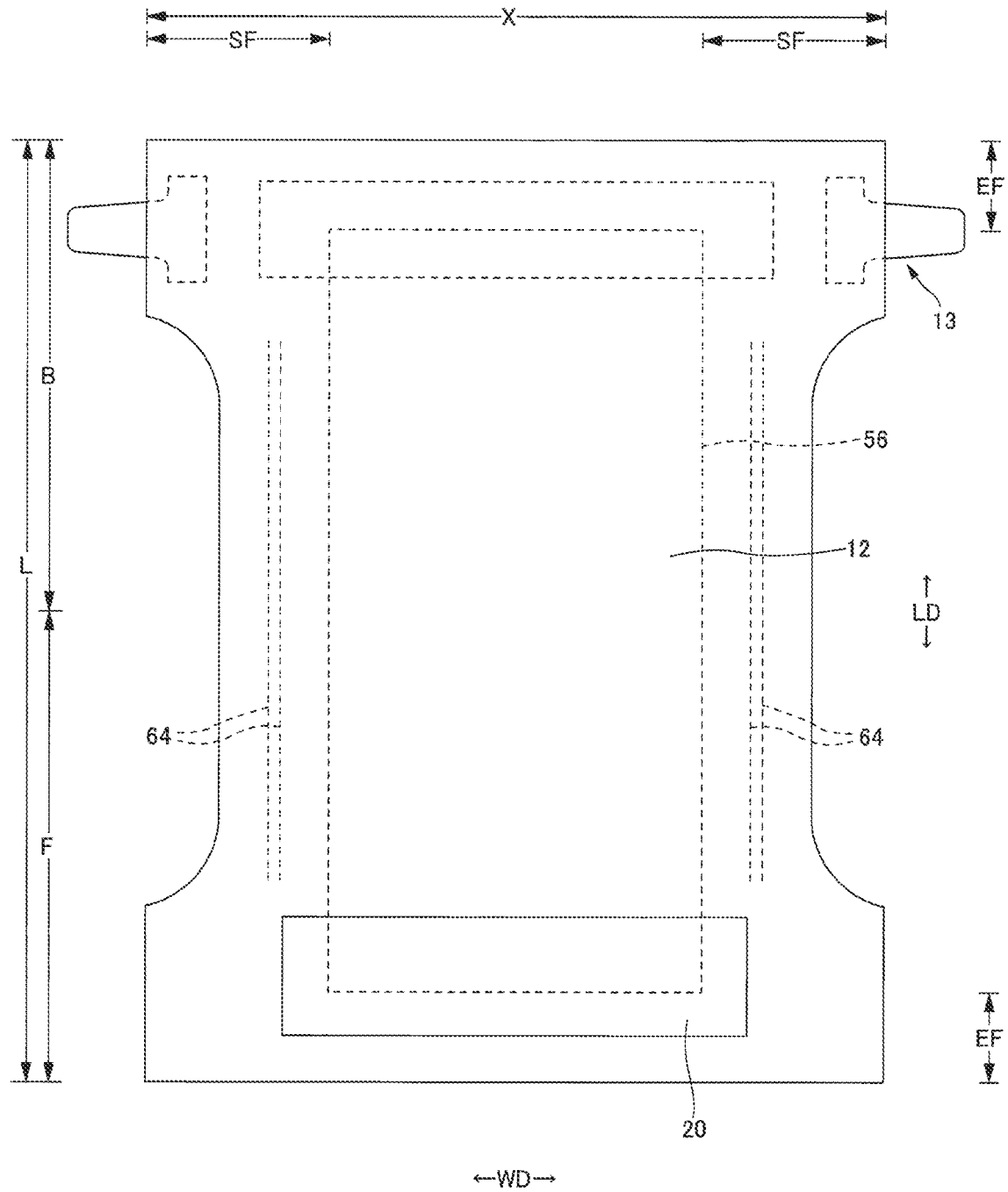

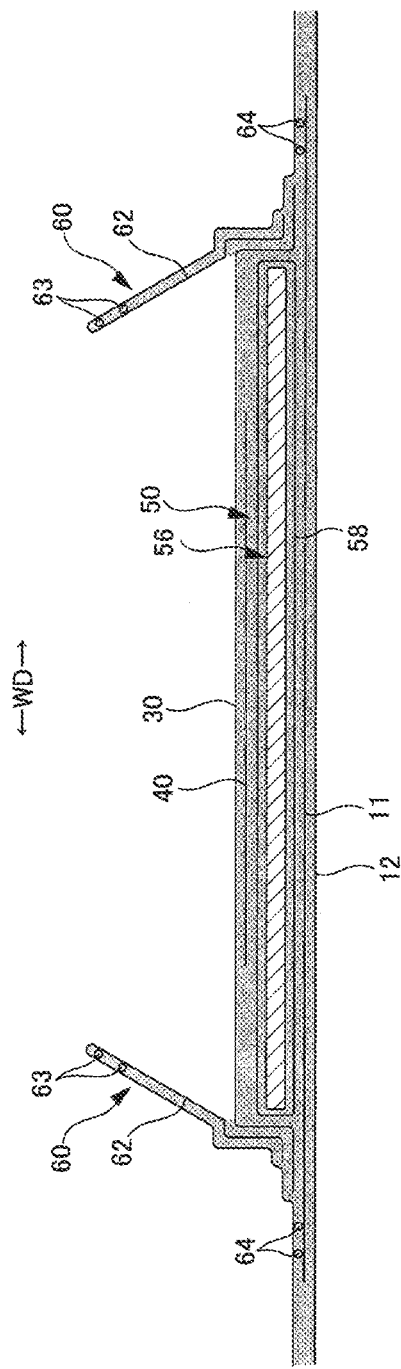

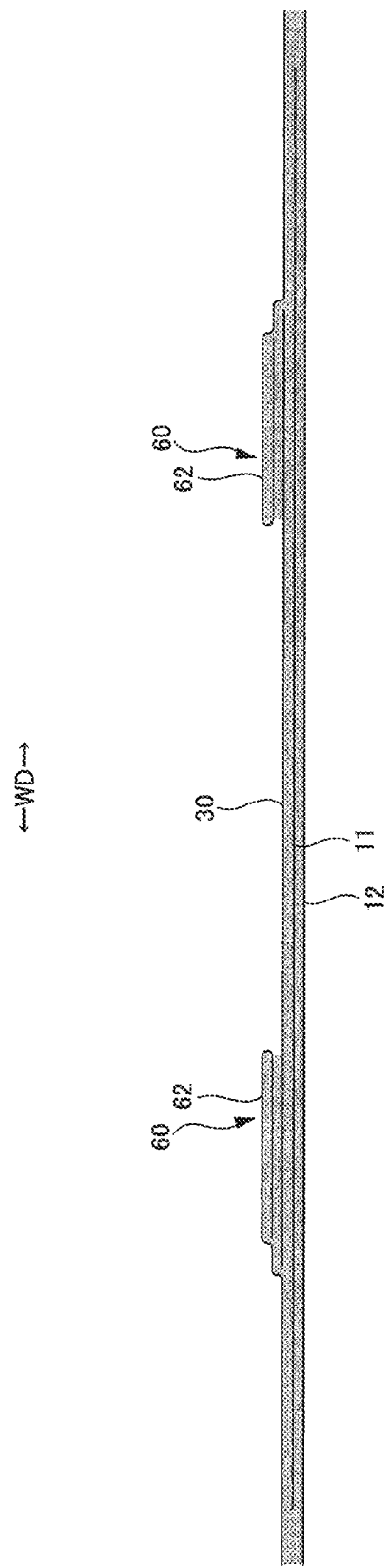

[FIG.5]
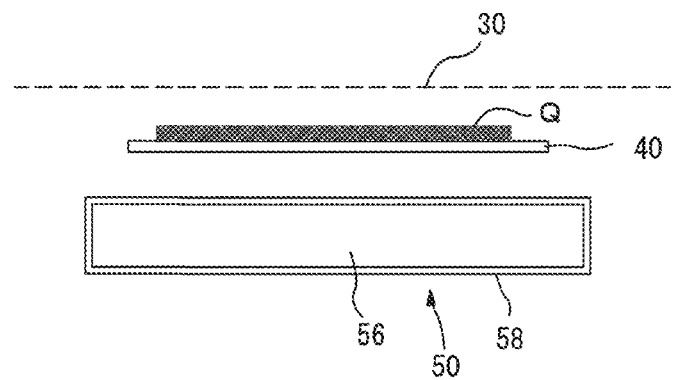

[FIG.6]
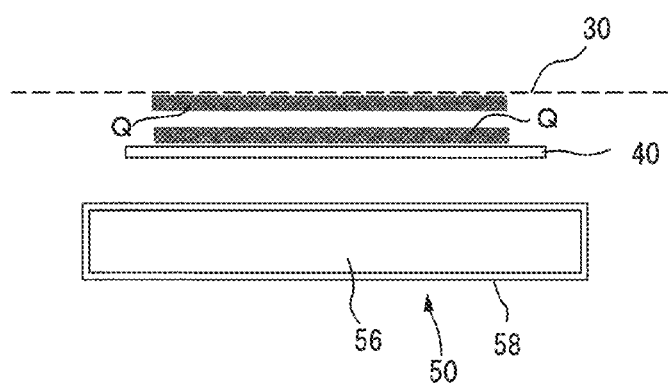

[FIG.7]
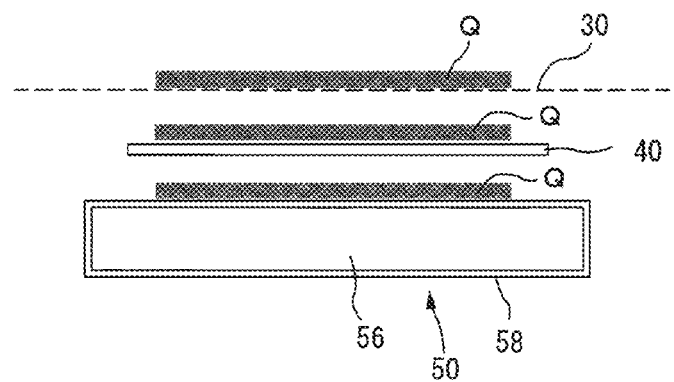

ABSORBENT ARTICLE

CROSS-REFERENCE TO RELATED APPLICATIONS

This application is the U.S. national stage application of International Application PCT/JP2020/002693, filed Jan. 27, 2020, which international application was published on Oct. 1, 2020, as International Publication WO 2020/195097 in the Japanese language. The International Application claims priority of Japanese Patent Application No. 2019-060524, filed Mar. 27, 2019. The international application and Japanese application are both incorporated herein by reference, in entirety.

TECHNICAL FIELD

The present invention relates to an absorbent article that absorbs a body fluid, particularly to a disposable diaper.

BACKGROUND ART

An absorbent article, particularly a disposable diaper often causes roughness of the skin of a wearer, particularly, rash disadvantageously.

Examples of a cause for this include friction with the skin at the time of wearing the diaper, and stimulation received by the skin from a body fluid and excreta (urine and loose stool) due to wearing the diaper for a long time.

In particular, the cause by stimulation due to contact of the skin with loose stool for a long time is large. In order to suppress this, the diaper needs to quickly absorb loose stool into an absorber. If the diaper can quickly absorb loose stool into the absorber, it is useful not only in reducing stimulation received by the skin but also in preventing leakage from a leg portion or a dorsal portion.

A first cause for hindering absorption of loose stool through a top sheet is that when a stool component passes through the top sheet, a component that cannot pass through the top sheet remains on a surface portion of fibers constituting the top sheet, and the top sheet is clogged. A second cause for hindering absorption of loose stool through the top sheet is that an excreta speed exceeds an absorption rate of the diaper, and loose stool cannot be absorbed and remains on the top sheet.

Remaining of a loose stool component on the top sheet may cause the loose stool component to slide on the top sheet, and may result in leakage of stool.

Therefore, it is very important for the diaper to quickly absorb loose stool into an absorber.

Patent Literature 1 discloses that a skin care agent is provided between so-called gather cuffs on both sides in the width direction of a diaper.

In addition, the skin care agent is provided on a top sheet, and for example, the skin care agent contains a diamide derivative as an active component.

CITATION LIST

Patent Literature

Patent Literature 1: JP 2018-102836 A

SUMMARY OF INVENTION

Technical Problem

However, the present inventor has found that there is a limit to suppressing roughness of the skin by the skin care agent, and it is more important to configure a diaper so as to quickly absorb loose stool into an absorber.

Therefore, a main object of the present invention is to provide an absorbent article that can prevent or suppress roughness of the skin of a wearer by configuring the absorbent article so as to quickly absorb a body fluid into an absorber (for example, configuring a diaper so as to quickly absorb loose stool into an absorber).

Solution to Problem

Main aspects of an absorbent article that has solved the above problem are as follows.
<First Aspect>
An absorbent article including a liquid-holding absorber and a liquid pervious top sheet on a skin-facing surface side of the absorber, in which an absorbent mainly containing glycerin is provided on an intermediate sheet that transfers at least a body fluid that has passed through the top sheet to the absorber.

As illustrated in Examples described later, it has been found that when an absorbent mainly containing glycerin is provided on an intermediate sheet that is disposed between the top sheet and the absorber and transfers a body fluid that has passed through the top sheet to the absorber, the body fluid (for example, loose stool) is quickly absorbed into the absorber.
<Second Aspect>
In a second aspect, the intermediate sheet includes a second sheet on the top sheet side and a wrapping sheet wrapping the absorber, and the absorbent is provided on the second sheet and the wrapping sheet.

The absorbent can be provided not only on the second sheet but also on the wrapping sheet wrapping the absorber.
<Third Aspect>
In a third aspect, the absorbent is provided also on a non-skin side surface of the top sheet.

It is considered that the absorbent provided on the non-skin side surface of the top sheet delivers a body fluid to the intermediate sheet side at a stage where the body fluid tries to pass through the top sheet, and therefore an effect of improving an absorption rate is enhanced.
<Fourth Aspect>
In a fourth aspect, the top sheet is formed of a nonwoven fabric having a large number of apertures.

Since the top sheet is formed of a nonwoven fabric having a large number of apertures, a body fluid is easily absorbed. As a result, an effect of improving an absorption rate by the absorbent according to the present invention is enhanced.
<Fifth Aspect>
In a fifth aspect, the absorbent contains 70% by mass or more of glycerin as a composition component, and contains one or more additives selected from the group consisting of an emulsifier, a phosphate, a paraffin, and a surfactant as an additive.

Advantageous Effects of Invention

The present invention can prevent or suppress roughness of the skin of a wearer by configuring an absorbent article so as to quickly absorb a body fluid into an absorber (for example, configuring a diaper so as to quickly absorb loose stool into an absorber).

BRIEF DESCRIPTION OF DRAWINGS

FIG. 1 is a plan view illustrating an internal surface of a tape-type disposable diaper in a state where the diaper is unfolded.

FIG. 2 is a plan view illustrating an outer surface of a tape-type disposable diaper in a state where the diaper is unfolded.

FIG. 3 is a cross-sectional view of a center of FIG. 1 in a front-back direction.

FIG. 4 is a cross-sectional view of an end portion of FIG. 1 in a front-back direction.

FIG. 5 is an explanatory view of a main portion of Example 1 of an embodiment.

FIG. 6 is an explanatory view of a main portion of Example 2 of the embodiment.

FIG. 7 is an explanatory view of a main portion of Example 3 of the embodiment.

DESCRIPTION OF EMBODIMENTS

<Configuration Example of Disposable Diaper>

A configuration example of a tape-type disposable diaper as an absorbent article of the present invention is illustrated in FIGS. 1 to 5.

An example of a disposable diaper is illustrated. In the drawings, a reference character X indicates the maximum width of the diaper excluding a connecting tape, a reference character L indicates the maximum length of the diaper, and a dotted pattern portion in a cross-sectional view indicates a hot melt adhesive as a bonding means for bonding constituent members located on a front surface side and a back surface side.

The hot melt adhesive can be applied by a known method such as slot application, bead application into a continuous line or dot shape, spray application into a spiral shape or a Z shape, or pattern coating (transfer of a hot melt adhesive by a letterpress method). Alternatively or in addition, in a fixing portion of an elastic member, the hot melt adhesive can be applied to an outer peripheral surface of the elastic member, and the elastic member can be fixed to an adjacent member. Examples of the hot melt adhesive include an EVA-based agent, a pressure sensitive adhesive rubber-based agent (elastomer-based agent), a polyolefin-based agent, and a polyester/polyamide-based agent, and these can be used without particular limitation. As a bonding means for bonding constituent members, a means by material welding such as heat sealing or ultrasonic sealing can also be used.

The tape-type disposable diaper includes a crotch portion including a center in a front-back direction LD, a ventral side portion F extending forward from the center in the front-back direction LD, and a dorsal side portion B extending backward from the center in the front-back direction LD.

This tape-type disposable diaper includes an absorber 56 incorporated in a range including the crotch portion, a liquid pervious top sheet 30 covering a front surface side of the absorber 56, a liquid impervious sheet 11 covering a back surface side of the absorber 56, and an exterior nonwoven fabric 12 covering a back surface side of the liquid impervious sheet and forming a product outer surface.

On the other hand, side flap portions SF not including the absorber 56 are formed on both sides in the width direction from the ventral side portion F to the dorsal side portion B, and each have a connecting tape 13 detachably connected to an outer surface of the ventral side portion F. In an attached state, the connecting tape 13 is connected to an outer surface of the ventral side portion F. In addition, the tape-type disposable diaper of the illustrated example has a pair of end flap portions EF extending to a front side and a back side of the absorber 56 and not including the absorber 56.

Hereinafter, a material of each portion and a characteristic part thereof will be described sequentially.

(Absorber)

The absorber 56 absorbs and holds an excrement liquid, and can be formed by an assembly of fibers. As this fiber assembly, in addition to those obtained by accumulating a short fiber such as fluff pulp or a synthetic fiber, a filament assembly obtained by opening a tow (fiber bundle) of a synthetic fiber such as cellulose acetate as necessary can also be used. In a case where fluff pulp or a short fiber is accumulated, a fiber basis weight may be, for example, about 100 to 300 g/m$^2$. In a case of a filament assembly, a fiber basis weight may be, for example, about 30 to 120 g/m$^2$. In a case of a synthetic fiber, a fineness is, for example, 1 to 16 dtex, preferably 1 to 10 dtex, and more preferably 1 to 5 dtex. In a case of a filament assembly, the filament may be formed of a non-crimped fiber but is preferably formed of a crimped fiber. The degree of crimp of the crimped fiber may be, for example, about 5 to 75, preferably 10 to 50, and more preferably 15 to 50 per 2.54 cm. In addition, a uniformly crimped fiber can be used.

(Super Absorbent Polymer Particles)

The absorber 56 may contain super absorbent polymer particles partially or entirely. The super absorbent polymer particles include "powder" in addition to "particles". As super absorbent polymer particles 54, those used for this type of absorbent article can be used as they are. The particle diameters of the super absorbent polymer particles are not particularly limited. However, for example, when sieving using a standard sieve of 500 μm (JIS Z8801-1: 2006) (shake for five minutes) is performed, and particles falling under the sieve using this sieving are sieved using a standard sieve of 180 μm (JIS Z8801-1: 2006) (shake for five minutes), it is desirable that a ratio of particles remaining on the standard sieve of 500 μm is 30% by weight or less, and a ratio of particles remaining on the standard sieve of 180 μm is 60% by weight or more.

A material of the super absorbent polymer particles can be used without particular limitation, but those having a water absorption capacity of 40 g/g or more are preferable. Examples of the super absorbent polymer particles include a starch-based material, a cellulose-based material, and a synthetic polymer-based material. A starch-acrylic acid (salt) graft copolymer, a saponified product of a starch-acrylonitrile copolymer, a cross-linked product of sodium carboxymethyl cellulose, an acrylic acid (salt) polymer, or the like can be used. As the shapes of the super absorbent polymer particles, a usually used particulate material shape is suitable, but other shapes can also be used.

As the super absorbent polymer particles, those having a water absorption rate of 70 seconds or less, particularly 40 seconds or less are suitably used. When the water absorption rate is too slow, so-called returning that a liquid supplied into the absorber 56 returns out of the absorber 56 tends to occur.

As the super absorbent polymer particles, those having a gel strength of 1000 Pa or more are suitably used. This makes it possible to effectively suppress a sticky feeling after liquid absorption even in a case of using the bulky absorber 56.

The basis weight of the super absorbent polymer particles can be appropriately determined depending on the absorption amount required for an application of the absorber 56. Therefore, the basis weight can be 50 to 350 g/m$^2$ although this cannot be applied generally. The basis weight of the polymer of less than 50 g/m$^2$ makes it difficult to secure the absorption amount. When the basis weight exceeds 350 g/m², not only the effect is saturated but also the excess of the super absorbent polymer particles imparts a gritty and uncomfortable feeling.

(Wrapping Sheet)

The absorber 56 can be incorporated as an absorbent element 50 wrapped in a wrapping sheet 58 in order to prevent escape of the super absorbent polymer particles or to improve shape maintenance of the absorber 56. As the wrapping sheet 58, tissue paper, particularly crepe paper, a nonwoven fabric, a polylaminated nonwoven fabric, a sheet with small holes, and the like can be used. However, it is desirable that the wrapping sheet 58 is a sheet from which super absorbent polymer particles do not escape. When a nonwoven fabric is used instead of crepe paper, a hydrophilic spunbonded/melt blown/melt blown/spunbonded (SMMS) nonwoven fabric is particularly suitable, and polypropylene, polyethylene/polypropylene, or the like can be used as a material thereof. A nonwoven fabric having a fiber basis weight of 5 to 40 g/m², particularly of 10 to 30 g/m² is desirable.

As illustrated in FIG. 3, the single wrapping sheet 58 may wrap the whole of the absorber 56, or a plurality of the wrapping sheets 58 such as upper and lower two wrapping sheets 58 may wrap the whole of the absorber 56. The wrapping sheet can be omitted.

(Top Sheet)

As the top sheet 30, a liquid pervious sheet, for example, a perforated or imperforated nonwoven fabric or a porous plastic sheet can be used. Among these materials, the nonwoven fabric is not particularly limited concerning a raw material fiber thereof. Examples thereof include a synthetic fiber such as a polyolefin-based fiber including polyethylene and polypropylene, a polyester-based fiber, or a polyamide-based fiber, a regenerated fiber such as rayon or cupra, a natural fiber such as cotton, and a mixed fiber and a composite fiber in which two or more kinds of these fibers are used. Furthermore, the nonwoven fabric may be manufactured by any processing. Examples of a processing method include known methods such as a spunlacing method, a spunbonding method, a thermal bond method, a melt blown method, a needle punching method, an air through method, and a point bond method. For example, if softness and drapeability are demanded, a spunlacing method is a preferable processing method. If bulkiness and softness are demanded, a thermal bond method is a preferable processing method.

The top sheet 30 extends from a front end to a back end of the product in the front-back direction and extends to a lateral side more than the absorber 56 in the width direction WD. For example, when a starting point of a rising gather 60 described later is located closer to the center in the width direction than a side edge of the absorber 56, appropriate deformation can be made, for example, the width of the top sheet 30 is made shorter than the maximum width of the absorber 56 as necessary.

(Intermediate Sheet)

In order to quickly transfer a liquid that has passed through the top sheet 30 to the absorber, it is possible to dispose an intermediate sheet (also referred to as "second sheet") 40 having a higher liquid permeation rate than the top sheet 30. The intermediate sheet 40 is used in order to rapidly transfer a liquid to the absorber to enhance absorption performance of the absorber, and to prevent a "returning" phenomenon of the absorbed liquid from the absorber. The intermediate sheet 40 can be omitted.

Examples of the intermediate sheet 40 include a similar material to that of the top sheet 30, a spunlaced nonwoven fabric, a spunbonded nonwoven fabric, an SMS nonwoven fabric, a pulp nonwoven fabric, a mixed sheet of pulp and rayon, a point bonded nonwoven fabric, and crepe paper. In particular, an air through nonwoven fabric is preferable because of being bulky. As the air through nonwoven fabric, a composite fiber having a core-sheath structure is preferably used. In this case, a resin used for the core may be polypropylene (PP) but is preferably polyester (PET) having high rigidity. The basis weight is preferably 17 to 80 g/m², and more preferably 25 to 60 g/m². A raw material fiber of the nonwoven fabric preferably has a fineness of 2.0 to 10 dtex. In order to make the nonwoven fabric bulky, as mixed fibers of all or some of raw material fibers, eccentric fibers having no core in the center, hollow fibers, eccentric and hollow fibers are also preferably used.

The intermediate sheet 40 in the illustrated example is disposed at the center so as to be shorter than the width of the absorber 56, but may be disposed over the maximum width. The intermediate sheet 40 may be disposed over the maximum length of the diaper, but may be disposed only in an intermediate portion including an excrement position as in the illustrated example.

(Liquid Impervious Sheet)

The liquid impervious sheet 11 is not particularly limited, but preferably has moisture permeability. As the liquid impervious sheet 11, for example, a microporous sheet obtained by kneading an inorganic filler in a polyolefin-based resin such as polyethylene or polypropylene, molding the kneaded mixture into a sheet, and then stretching the sheet in a monoaxial or biaxial direction can be suitably used. In addition, as the liquid impervious sheet 11, a sheet in which a nonwoven fabric is used as a base material and waterproofness thereof is enhanced can also be used.

It is desirable that the liquid impervious sheet 11 extends within the same range as or a wider range than the absorber 56 in the front-back direction LD and the width direction WD. However, for example, when another water blocking means is present, an end portion of the absorber 56 does not have to be covered in the front-back direction LD and the width direction WD as necessary.

(Exterior Nonwoven Fabric)

The exterior nonwoven fabric 12 covers the entire back surface side of the liquid impervious sheet 11 and imparts a cloth-like appearance to a product outer surface. The exterior nonwoven fabric 12 is not particularly limited. Examples thereof as a material fiber include a synthetic fiber such as a polyolefin-based fiber including polyethylene and polypropylene, a polyester-based fiber, or a polyamide-based fiber, a regenerated fiber such as rayon or cupra, and a natural fiber such as cotton. Examples of a processing method include a spunlacing method, a spunbonding method, a thermal bond method, an air through method, and a needle punching method. However, a long-fiber nonwoven fabric such as a spunbonded nonwoven fabric, an SMS nonwoven fabric, or an SMMS nonwoven fabric is suitable from a viewpoint of achieving both texture and strength. A nonwoven fabric can be used in a single sheet or in a laminate of a plurality of sheets. In the latter case, the nonwoven fabrics are preferably bonded to each other with a hot melt adhesive or the like. In a case where a nonwoven fabric is used, it is desirable that the nonwoven fabric has a fiber basis weight of 10 to 50 g/m², particularly 15 to 30 g/m².

(Rising Gather)

In order to block excrement that moves laterally on the top sheet 30 and to prevent so-called side leakage, rising gathers 60 rising on a skin side of a wearer are preferably disposed on both sides of a surface in the width direction WD. Of course, the rising gathers 60 can be omitted.

When the rising gather 60 is adopted, a structure thereof is not particularly limited, and any known structure can be adopted. The rising gather 60 in the illustrated example includes a gather sheet 62 substantially continuous in the width direction WD, and an elongated gather elastic member 63 fixed to the gather sheet 62 in a stretched state in the front-back direction LD. A water repellent nonwoven fabric can be used as the gather sheet 62, and a rubber thread or the like can be used as the gather elastic member 63. As illustrated in FIGS. 1 and 2, a plurality of elastic members may be disposed, or one elastic member may be disposed.

An internal surface of the gather sheet 62 has a bonding start edge in the width direction WD on a side portion of the top sheet 30. A portion from the bonding start edge to the outside in the width direction is bonded to an internal surface of each side flap portion SF, that is, in the illustrated example, bonded to a side portion of the liquid impervious sheet 11 and a side portion of the exterior nonwoven fabric 12 located in an outside thereof in the width direction with a hot melt adhesive or the like.

In a periphery of a leg, a portion from the bonding start edge of the rising gather 60 to the inside in the width direction is fixed to the top sheet 30 at both end portions in a product front-back direction. However, a portion therebetween is a non-fixed free portion, and the free portion rises by a contraction force of the elastic member 63 and comes into close contact with a body surface.

(Plane Gather)

To each side flap portion SF, a side elastic member 64 formed of an elongated elastic member such as a rubber thread is fixed in a stretched state in the front-back direction LD, and a periphery of a leg of each side flap portion SF is configured as a plane gather. The leg periphery elastic member 64 can be disposed between the gather sheet 62 and the liquid impervious sheet 11 outside the vicinity of the bonding start edge in the width direction in the bonded portion of the gather sheet 62 as in the illustrated example, and can also be disposed between the liquid impervious sheet 11 and the exterior nonwoven fabric 12 in the side flap portion SF. A plurality of the leg periphery elastic members 64 may be disposed on each side as in the illustrated example, or only one leg periphery elastic member 64 may be disposed on each side.

(Connecting Tape)

In the dorsal side portion B, the connecting tape 13 to be detachably connected to an outer surface of the ventral side portion F as a connecting means is disposed. When the diaper is worn, the connecting tapes 13 are extended from both sides of a waist to an outer surface of the ventral side portion F, and the connecting portions 13A of the connecting tapes 13 are connected to appropriate positions of the outer surface of the ventral side portion F.

The structure of the connecting tape 13 is not particularly limited, but includes a tape main unit section protruding from a tape attachment portion 13C and a connecting portion 13A disposed at an intermediate portion in the width direction, and a tip side of the connecting portion 13A is a tab part. The shape of the connecting tape 13 is not particularly limited, either. However, the tape attachment portion 13C may have a portion having the longest and constant size in the front-back direction, and the tape main unit section may have a tapered shape in which the tape main unit section becomes thinner toward a tip.

As the connecting portion 13A, a hook member (male member) of a mechanical fastener (hook and loop fastener) or an adhesive layer may be disposed. The hook member has many engaging projections on a connecting surface thereof. Examples of the shapes of the engaging projections include (A) tick shape, (B) J shape, (C) mushroom shape, (D) T shape, and (E) double J shape (a shape in which the J-shaped ones are connected to each other back to back), but any shape may be used.

As the sheet base material forming from the tape attachment portion 13C to the tape main unit section, a nonwoven fabric, a plastic film, a polylaminated nonwoven fabric, paper, or a composite material thereof can be used. However, a spunbonded nonwoven fabric, an air through nonwoven fabric, or a spunlaced nonwoven fabric having a fineness of 1.0 to 3.5 dtex, a basis weight of 20 to 100 $g/m^2$, and a thickness of 1 mm or less is preferable.

(Target Portion)

A target portion is preferably disposed at a connecting part for the connecting tape 13 in the ventral side portion F. As in the illustrated example, the target portion can be disposed by attaching a target sheet 20 for facilitating connection to an outer surface of the ventral side portion F. In a case where the connecting portion 13A is formed of a hook member, as the target sheet 20, it is possible to use one in which many loop threads making engaging projections of the hook member entangled therewith are disposed on a surface of a sheet base material formed of a plastic film or a nonwoven fabric. In a case where the connecting portion 13A is formed of an adhesive layer, as the target sheet 20, it is possible to use one obtained by subjecting a surface of a sheet base material formed of a plastic film having a smooth surface with high pressure sensitive adhesiveness to a peeling treatment. When the connecting part for the connecting tape 13 in the ventral side portion F is formed of a nonwoven fabric, for example, when the exterior nonwoven fabric 12 is disposed as in the illustrated example, the target sheet 20 can be omitted, and the hook member can be entangled with fibers of the exterior nonwoven fabric 12 to be connected. In this case, in addition to disposing the target sheet 20 as a mark between the exterior nonwoven fabric 12 and the liquid impervious sheet 11, a mark may be printed on an outer surface of the exterior nonwoven fabric 12 or the liquid impervious sheet 11.

<Absorbent>

Next, an embodiment of the present invention will be described.

In the embodiment, an absorbent mainly containing glycerin is provided on an intermediate sheet that transfers a body fluid that has passed through a top sheet to an absorber.

As illustrated in Examples described later, when an absorbent mainly containing glycerin is provided on an intermediate sheet that is disposed between a top sheet and an absorber and transfers a body fluid that has passed through the top sheet to an absorber, the body fluid (for example, loose stool) is quickly absorbed into the absorber.

As a representative example, as illustrated in FIG. 5 schematically illustrating only a main part, an absorbent Q mainly containing glycerin is provided on the intermediate sheet 40 that transfers a body fluid that has passed through the top sheet 30 to the absorber 56.

The intermediate sheet according to the present invention refers to the second sheet 40 located on the top sheet 30 side indicated by reference character 40 in FIGS. 5 to 7.

In addition to providing the absorbent Q on the second sheet 40, the absorbent Q can be provided on the top sheet 30.

In this case, it is desirable that the absorbent Q is provided on a non-skin side surface (lower surface in FIG. 6) of the top sheet 30 as illustrated in FIG. 6 instead of providing the absorbent Q on a skin side surface of the top sheet 30.

The skin side surface (upper surface in FIG. 6) of the top sheet 30 is preferably hydrophobic in order to enhance diffusibility of a liquid component of a body fluid. However, if a hydrophilic absorbent mainly containing glycerin is provided, the hydrophobicity of the top sheet 30 is hindered. Therefore, this form is not so preferable.

On the other hand, if the absorbent Q is provided on the non-skin side surface (lower surface in FIG. 6) of the top sheet 30, it is considered that the absorbent Q provided on the non-skin side surface of the top sheet 50 is delivered to the intermediate sheet 40 side at a stage where a body fluid tries to pass through the top sheet 50, and therefore an effect of improving an absorption rate is enhanced.

Since the top sheet 30 is formed of a nonwoven fabric having a large number of apertures, a body fluid is easily absorbed. As a result, an effect of improving an absorption rate by the absorbent Q is enhanced.

The aperture of the nonwoven fabric can have an appropriate shape such as a circle or an ellipse. It is desirable that the aperture size (equivalent diameter in a case of an ellipse) is 0.1 to 2.0 mm. The apertures are arranged in, for example, a zigzag shape or a lattice shape. It is desirable that an opening ratio is 2 to 40%. When the aperture size and the opening ratio are small, permeability of a body fluid tends to be insufficient. When the aperture size and the opening ratio are excessively large, returning that a body fluid once absorbed by an absorbent element returns to a surface of the top sheet may occur.

As described above, the intermediate sheet according to the present invention refers to the second sheet 40 located on the top sheet 30 side. The absorbent Q can be provided on the skin side surface of the wrapping sheet 58.

Under this aspect, as illustrated in FIG. 7, the absorbent Q can be further provided on the top sheet 30, preferably on the non-skin side surface thereof.

When the absorbent Q is provided on each of a plurality of sheets, it is desirable to form a gradient, for example, as follows to the application amount of the absorbent Q. This aspect is preferable because the gradient of the application amount relates to a transfer rate of a body fluid by the absorbent Q.

Top sheet<<Intermediate sheet<Wrapping sheet

For example, in a case of the intermediate sheet 40, the application amount is preferably 0.02 g/m$^2$ or more, more preferably 0.05 g/m$^2$ or more, preferably 3.00 g/m$^2$ or less, more preferably 1.50 g/m$^2$ or less, and specifically preferably 0.05 g/m$^2$ or more and 1.20 g/m$^2$ or less.

The absorbent according to the present invention may contain 70% by mass or more, preferably 85% by mass or more of glycerin as a composition component, and may contain one or more additives selected from the group consisting of an emulsifier, a phosphate, a glycerin fatty acid ester, a paraffin, and a surfactant as an additive.

As the surfactant, an ether type nonionic surfactant and a nonionic surfactant containing an EO/PO type are preferable.

In providing the absorbent, when the top sheet and the intermediate sheet are bonded to each other in a stripe shape or a spiral shape by a hot melt adhesive, application in a stripe shape extending in the front-back direction at intervals in the width direction of the absorbent article is preferable. When the top sheet and the intermediate sheet are bonded to each other by thermal embossing, spray coating may be performed to the entire surface of a target region in addition to a stripe shape or a spiral shape.

On the other hand, when the absorbent is provided on the non-skin side surface of the top sheet 30, for example, the absorbent may be applied only to the intermediate sheet 40, and a part of the absorbent may be transferred to the non-skin side surface of the top sheet 30 using a compressive force received at the time of wrapping or storing the absorbent article or a compressive force at the time of use of a wearer to be applied.

Next, Example will be described.

(Experimental Example 1)

Under configurations of three types of disposable diapers having different forms of providing the absorbent Q as illustrated in FIGS. 5, 6, and 7, each of the configurations having the structure illustrated in FIGS. 1 to 4, pseudo loose stool was caused to flow down from above the top sheet having apertures, and absorption characteristics were examined. Note that a disposable diaper on which no absorbent was provided was also prepared and used as Comparative Example.

For each of a total of four types of disposable diapers, five samples were prepared, and an absorption test was performed.

In the specific absorption test, a disposable diaper was formed into an unfolded state. A tube having a diameter of 7 cm was placed on the dorsal side of the disposable diaper. A time point when 20 ml of pseudo loose stool started to be caused to flow in the diaper was defined as a start point of measurement of an absorption rate. Pseudo loose stool starts to pass through the top sheet from the tube through an opening of a flat plate. 30 seconds after the start of the measurement of the absorption rate, the tube is removed. The time point when it is confirmed that moisture on a surface of the top sheet has disappeared is defined as end of the measurement of the absorption rate.

3 minutes after the start of inflow of pseudo loose stool, 10 sheets of filter paper of 10 cm×10 cm are stacked on the dorsal side of the disposable diaper, a weight of 1 kg of 10 cm×10 cm is placed thereon, and a weight increase due to absorption of a liquid transferred to the filter paper side 60 seconds later is defined as a returning amount.

Thereafter, the disposable diaper was disassembled. A measurement region having 8 cm in the width direction×15 cm in the front-back direction where the absorber on the dorsal side existed was cut out. A weight increase due to absorption of the liquid was calculated for each of the absorber, the wrapping sheet, the intermediate sheet (second sheet), and the top sheet. In this case, since the weight of the measurement region is known, the weight increase can be calculated.

As the pseudo loose stool, known yogurt-based pseudo loose stool was used. Here, pseudo loose stool obtained by mixing a commercially available yogurt and deionized water at a mass ratio of 2:3 and adjusting the viscosity to 300 mPa·s was used.

Results of the absorption test for the four types of disposable diapers are illustrated in Table 1.

TABLE 1

|  | Absorption rate (second) | Returning amount (g) | Top sheet absorption amount (g) | Second sheet absorption amount (g) |
|---|---|---|---|---|
| Comparative Example 1 (no absorbent) | 106 | 2.11 | 1.32 | 0.02 |
| Example 1 (form of FIG. 5) | 82 | 1.41 | 1.23 | 0.15 |

TABLE 1-continued

| | Absorption rate (second) | Returning amount (g) | Top sheet absorption amount (g) | Second sheet absorption amount (g) |
|---|---|---|---|---|
| Example 2 (form of FIG. 6) | 79 | 1.53 | 1.10 | 0.16 |
| Example 3 (form of FIG. 7) | 71 | 1.36 | 1.02 | 0.18 |

From these results, it has been found that application of the absorbent according to the present invention to the intermediate sheet makes the disposable diaper quickly absorb loose stool into the absorber, and is effective for making it difficult for loose stool to remain on a surface.

Results of the absorption test obtained by changing the type of the absorbent are illustrated in Table 2. The results of Example 1 are listed again in Table 2. As a comparison of the absorbent Q different from glycerin, in Comparative Example 2, an ether type nonionic surfactant is applied in the form of FIG. 5. In Comparative Example 3, a nonionic surfactant containing an EO/PO type is applied in the form of FIG. 5.

TABLE 2

| | Absorption rate (second) | Returning amount (g) | Top sheet absorption amount (g) | Second sheet absorption amount (g) |
|---|---|---|---|---|
| Example 1 (form of FIG. 5) | 82 | 1.41 | 1.23 | 0.15 |
| Comparative Example 2 (form of FIG. 5) | 87 | 1.67 | 1.20 | 0.13 |
| Comparative Example 3 (form of FIG. 5) | 92 | 1.92 | 1.52 | 0.23 |

From these results, it has been found that the absorbent according to the present invention has a higher absorption rate and is less likely to cause loose stool to remain on a surface than those used as a hydrophilic surfactant in this technical field.

<Explanation of Terms in Specification>

The following terms in the specification have the following meanings unless otherwise specified in the specification.

Reference character "LD" indicates a front-back direction of an absorbent article, and WD indicates a width direction thereof. The front-back direction and the width direction are orthogonal to each other.

"Unfolded state" means a flatly unfolded state without contraction or slackness.

"Basis weight" is measured as follows. A sample or a test piece is predried and then left in a test chamber or an apparatus in a standard state (test location is at a temperature of 23±1° C. and a relative humidity of 50±2%) so as to have a constant weight. Predrying refers to causing a sample or a test piece to have a constant weight in an environment of a temperature of 100° C. Note that fibers having an official moisture regain of 0.0% do not have to be predried. A sample of 100 mm×100 mm in size is cut out from a test piece having a constant weight using a template for sampling (100 mm×100 mm). The weight of the sample is measured. The weight is multiplied by 100 to calculate the weight per square meter to be used as a basis weight.

When environmental conditions in a test and a measurement are not described, the test and the measurement are performed in a test room or an apparatus in a standard state (test location is at a temperature of 23±1° C. and a relative humidity of 50±2%).

INDUSTRIAL APPLICABILITY

The present invention can be used for a general disposable wearable article, for example, various disposable diapers such as an underpants-type and pad-type disposable diapers, a sanitary napkin, and disposable wearable articles for swimming and playing in water in addition to the tape-type disposable diaper as in the above example.

REFERENCE SIGNS LIST

10 Edge around leg
11 Liquid impervious sheet
12 Exterior nonwoven fabric
13 Connecting tape
20 Target sheet
30 Top sheet
40 Intermediate sheet
50 Absorbent element
56 Absorber
58 Wrapping sheet
60 Rising gather
62 Gather sheet
B Dorsal side portion
F Ventral side portion
WD Width direction
LD Front-back direction
SF Side flap portion
Q Absorbent.

The invention claimed is:

1. A disposable diaper comprising:
a liquid-holding absorber; and
a liquid pervious top sheet on a skin-facing surface side of the absorber, wherein an intermediate sheet formed of an air through nonwoven fabric is provided in the middle between the liquid pervious top sheet and the liquid-holding absorber, which transfers a body fluid that has passed through the liquid pervious top sheet to the absorber,
the liquid pervious top sheet is formed by a hydrophobic nonwoven fabric on a skin side surface, the nonwoven fabric has a plurality of apertures, an aperture size for each of the plurality of apertures is 0.1 to 2.0 mm and an opening ratio of each of the plurality of apertures is 2 to 40%,
an absorbent containing glycerin is provided on a skin side surface of the liquid pervious top sheet, a skin side surface of the intermediate sheet, and a skin side surface of a wrapping sheet wrapping the liquid-holding absorber,
an application amount of the absorbent has a gradient that increases in the order of the skin side surface of the liquid pervious top sheet, the skin side surface of the intermediate sheet, and the skin side surface of the wrapping sheet wrapping the liquid-holding absorber, and
the application amount of the absorbent on the skin side surface of the intermediate sheet is 0.02 g/m$^2$ to 3.00 g/m$^2$.

2. The disposable diaper according to claim 1, wherein the absorbent contains 70% by mass or more of glycerin as a composition component, and contains one or more additives selected from the group consisting of an emulsifier, a phosphate, a paraffin, and a surfactant as an additive.

* * * * *